US010232027B2

(12) United States Patent
Karsi et al.

(10) Patent No.: US 10,232,027 B2
(45) Date of Patent: Mar. 19, 2019

(54) LIVE ATTENUATED *EDWARDSIELLA ICTALURI* VACCINE AND METHOD OF USING THE SAME

(71) Applicants: Attila Karsi, Starkville, MS (US); Mark L. Lawrence, Starkville, MS (US); Hossam Abdelhamed, Starkville, MS (US)

(72) Inventors: Attila Karsi, Starkville, MS (US); Mark L. Lawrence, Starkville, MS (US); Hossam Abdelhamed, Starkville, MS (US)

(73) Assignee: MISSISSIPPI STATE UNIVERSITY, Mississippi State, MS (US)

( * ) Notice: Subject to any disclaimer, the term of this patent is extended or adjusted under 35 U.S.C. 154(b) by 0 days.

(21) Appl. No.: 15/257,607

(22) Filed: Sep. 6, 2016

(65) Prior Publication Data
US 2017/0065695 A1    Mar. 9, 2017

Related U.S. Application Data

(60) Provisional application No. 62/213,939, filed on Sep. 3, 2015.

(51) Int. Cl.
| A61K 39/02 | (2006.01) |
| A61K 49/00 | (2006.01) |
| A61K 39/00 | (2006.01) |
| C07K 14/195 | (2006.01) |
| C12N 1/36 | (2006.01) |

(52) U.S. Cl.
CPC .......... *A61K 39/025* (2013.01); *C07K 14/195* (2013.01); *C12N 1/36* (2013.01); *A61K 2039/522* (2013.01); *A61K 2039/54* (2013.01); *A61K 2039/552* (2013.01); *A61K 2039/57* (2013.01)

(58) Field of Classification Search
CPC ................................ A61K 39/00; A61K 39/02
USPC ............................. 424/9.1, 9.2, 184.1, 234.1
See application file for complete search history.

(56) References Cited

PUBLICATIONS

Williams, M.L., Dissertation Abstgracts International, vol. 64, No. 9B, 2003.*
Rao, P.S.S., et al. ,Molecular Microbiology, 53(2):573-586, Jul. 2004.*

* cited by examiner

*Primary Examiner* — Rodney P Swartz
(74) *Attorney, Agent, or Firm* — Butler Snow LLP

(57) ABSTRACT

A live attenuated *Edwardsiella ictaluri* bacterium lacking a viable gene encoding a functional evpB protein and a method of using the same to protect fish against infection from virulent *Edwardsiella ictaluri*. The methods and compositions for protecting fish against infection from virulent *Edwardsiella ictaluri* comprising administering to a fish a therapeutically effective amount of an attenuated *Edwardsiella ictaluri* bacterium lacking a viable gene encoding a functional EvpB protein. The bacterium may include an insertion and/or deletion mutation in the evpB gene. The fish include catfish, preferably catfish fingerling or a catfish fry. The composition may be delivered via immersion delivery, an injection delivery, an oral delivery, or combinations thereof.

7 Claims, 11 Drawing Sheets
Specification includes a Sequence Listing.

LIVE ATTENUATED *EDWARDSIELLA ICTALURI* VACCINE AND METHOD OF USING THE SAME

CROSS-REFERENCE TO RELATED APPLICATIONS

This application claims priority to U.S. Provisional Application No. 62/213,939 to Attila Karsi et al. filed on Sep. 3, 2015, the contents of which are incorporated herein by reference in its entirety.

FIELD OF THE INVENTION

This invention was made with government support under grant number 2007-35204-18404 and 2014-70007-22359 awarded by the National Institute of Food and Agriculture (NIFA), USDA. The government has certain rights in the invention.

FIELD OF THE INVENTION

The presently-disclosed subject matter relates to a live attenuated bacterium and method of using the same. More particularly, the presently-disclosed subject matter relates to a live attenuated *Edwardsiella ictaluri* bacterium lacking a viable evpB gene and a method of using the same to protect fish against infection from virulent *Edwardsiella ictaluri*.

BACKGROUND OF THE INVENTION

*Edwardsiella ictaluri*, a Gram-negative rod, is the etiological agent of enteric septicemia (ESC) of catfish (Hawke, 1979). ESC is one of the most prevalent diseases of farmed channel catfish (*Ictalurus punctatus*), which is the largest aquaculture industry in the United States. ESC occurs in two forms: acute enteric septicemia and a chronic encephalitis (Shotts et al., 1986).

Although oxytetracycline, sulphadimethoxine/ormetoprim, and florfenicol are approved antibiotics in the United State for treatment of ESC in food fish, there are reports of bacterial resistance to antibiotics (Plumb et al., 1995; Smith et al., 1994). Also, anorexia is one of the earliest clinical signs of ESC. Therefore, these antibiotics are more effective in limiting the spread of an outbreak than in treating the disease. An alternative strategy for preventing ESC would be beneficial to the industry.

Vaccination is an efficient method for prevention and control of ESC. *Edwardsiella ictaluri* is a candidate for the development of a live attenuated vaccine due to the antigenic homogeneity of all *Edwardsiella ictaluri* isolates (Bertolini et al., 1990; Plumb and Vinitnantharat, 1989). There is a commercial vaccine for ESC (RE-33, commercial brand name AQUAVAC-ESC), which is developed by serial passage in increasing concentration of rifampicin resistance. Fry as young as 7 d post-hatch, developed an immune response when vaccinated with Aqua AQUAVAC-ESC (Klesius and Shoemaker, 1999). However, this vaccine is rifampicin resistant and antibiotic resistance is not a desired trait in a live attenuated vaccine. In addition, the genetic alteration or reason for attenuation in AQUAVAC-ESC is not unknown completely (Klesius and Shoemaker, 1997). Despite the availability of AQUAVAC-ESC and several previous attempts to develop an immersion-oral *Edwardsiella ictaluri* vaccine, however, ESC is still one of the most prevalent diseases threat to the catfish industry. Therefore, there is an urgent need for an effective vaccine that can prevent ESC and can be safely delivered to catfish fry before their release into production ponds.

SUMMARY OF THE INVENTION

An aspect of the present invention is to provide an attenuated *Edwardsiella ictaluri* bacterium lacking a viable gene encoding a functional EvpB protein. In some embodiments, the live attenuated bacterium contains a mutant evpB gene. In some embodiments, the mutation in the evpB gene is an insertion and/or a deletion mutation. In some embodiments, the mutation in the evpB gene is an in-frame deletion.

Another aspect of the invention is to provide methods and compositions for a vaccine for protecting fish against the against *Edwardsiella ictaluri* infection. The vaccine includes an immunogenically-effective amount of an attenuated *Edwardsiella ictaluri* bacterium described herein. In some embodiments, the fish is a catfish, such as, in some embodiments, a catfish fingerling or a catfish fry.

Another aspect of the invention is to provide a composition that includes a live attenuated *Edwardsiella ictaluri* bacterium where, in some embodiments, the bacterium lacks a viable gene encoding a functional EvpB protein. In some embodiments, the live attenuated bacterium contains a mutant evpB gene. In some embodiments, the mutation in the evpB gene is an insertion and/or a deletion mutation. In some embodiments, the mutation in the evpB gene is an in-frame deletion. In some embodiments, the composition includes an amount of the bacterium sufficient for protecting fish against infection from virulent *Edwardsiella ictaluri*. In some embodiments, in addition to an effective amount of the attenuated bacterium described above, the composition also contains a pharmaceutically-acceptable vehicle, carrier, or excipient. In this regard, in some embodiments, the composition is formulated for delivery to fish by immersion, injection, oral delivery, or combinations thereof.

In still another aspect, the present invention provides a method for protecting fish against infection from virulent *Edwardsiella ictaluri*, comprising administering to a fish a therapeutically effective amount of an attenuated *Edwardsiella ictaluri* bacterium lacking a viable gene encoding a functional EvpB protein. The administering step may be accomplished by immersion delivery, injection delivery, oral delivery, and combinations thereof. In preferred embodiments, the fish include catfish. In other preferred embodiments, the bacterium is mixed with a fish feed to form a fish feed mixture, and the fish feed mixture is delivered to the fish for oral consumption.

In still another aspect, the present invention provides a modified bacterium lacking a viable gene encoding a functional EvpB protein. In some embodiments, the modified bacterium contains a mutant evpB gene. In some embodiments, the mutation in the evpB gene is an insertion and/or a deletion mutation. In some embodiments, the mutation in the evpB gene is an in-frame deletion.

BRIEF DESCRIPTION OF THE DRAWINGS

Further advantages of the invention will become apparent by reference to the detailed description of preferred embodiments when considered in conjunction with the drawings which form a portion of the disclosure and wherein.

DETAILED DESCRIPTION

Figure 1:
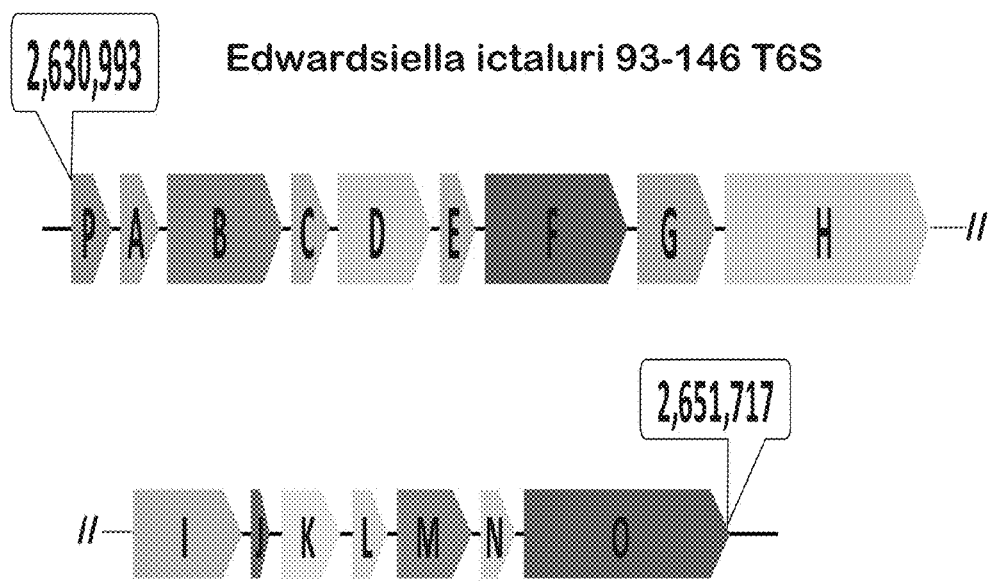
FIG. 1 is a diagram showing Type VI secretion system organization in the *Edwardsiella ictaluri* genome. The arrows indicate the direction of transcription and numbers at the beginning and at the end indicate genomic coordinates.

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

Each example is provided by way of explanation of the present disclosure and is not a limitation thereon. In fact, it will be apparent to those skilled in the art that various modifications and variations can be made to the teachings of the present disclosure without departing from the scope of the disclosure. For instance, features illustrated or described as part of one embodiment can be used with another embodiment to yield a still further embodiment.

While the terms used herein are believed to be well understood by one of ordinary skill in the art, definitions are set forth herein to facilitate explanation of the presently-disclosed subject matter.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a", "an", and "the" refer to "one or more" when used in this application, including the claims. Thus, for example, reference to "a cell" includes a plurality of such cells, and so forth.

All references to singular characteristics or limitations of the present disclosure shall include the corresponding plural characteristic(s) or limitation(s) and vice versa, unless otherwise specified or clearly implied to the contrary by the context in which the reference is made.

All combinations of method or process steps as used herein can be performed in any order, unless otherwise specified or clearly implied to the contrary by the context in which the referenced combination is made.

The methods and compositions of the present disclosure, including components thereof, can comprise, consist of, or consist essentially of the essential elements and limitations of the embodiments described herein, as well as any additional or optional components or limitations described herein or otherwise useful.

Unless otherwise indicated, all numbers expressing quantities of ingredients, properties such as reaction conditions, and so forth used in the specification and claims are to be understood as being modified in all instances by the term "about." Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

The type VI secretion system (T6SS) is a recently identified key virulence factor for many important pathogenic bacteria. This system is highly conserved and widely distributed in Gram-negative bacteria, which has been identified in more than 25% of Gram-negative bacteria as one or more copies. The T6SS delivers protein effectors into the periplasm of the target cells directly upon cell-to-cell contact and, therefore, contributes to different processes ranging from inter-bacterial killing to pathogenesis. The number of genes encoded within T6SS clusters usually varies between 16 and 38 genes, with a minimal set of 13 genes required to assemble a functional T6SS. The T6SS is also required to kill other bacterial cells by secreting anti-bacterial proteins.

Using a comparative proteomics approach, several important virulence genes from T6SS and type III secretion system (T3SS) of *Edwardsiella ictaluri* have been identified. Also, proteomics studies have shown that EvpB protein is differentially regulated during in vitro iron-restricted conditions. In this regard, and without wishing to be bound by any particular theory, it was believed that EvpB protein was a target member in the T6SS of *Edwardsiella ictaluri*, and that deletion of the evpB gene would attenuate *Edwardsiella*

*ictaluri* in catfish. As such, the presently-disclosed subject matter is based, at least in part, on the discovery that an evpB mutant can be used as a live attenuated vaccine against ESC, that such a mutant is safe in catfish and efficacious against *Edwardsiella ictaluri* WT infections, and that such an evpB mutant can be produced by in-frame allelic exchange for use as a vaccine in catfish fry and fingerlings.

The presently-disclosed subject matter thus relates to live attenuated bacteria and methods of using the same. More particularly, the presently-disclosed subject matter relates to a live attenuated *Edwardsiella ictaluri* bacterium lacking a viable evpB gene and a method of using the same to protect fish against infection from virulent *Edwardsiella ictaluri*.

In some embodiments of the presently-disclosed subject matter, an attenuated *Edwardsiella ictaluri* bacterium is provided. In some embodiments, the bacterium lacks a viable gene encoding a functional EvpB protein. The term "gene" is used broadly herein to refer to segments of DNA associated with a biological function. Thus, genes include, but are not limited to, coding sequences and/or the regulatory sequences required for their expression. Genes can also include non-expressed DNA segments that, for example, form recognition sequences for a polypeptide. Genes can be obtained from a variety of sources, including cloning from a source of interest or synthesizing from known or predicted sequence information, and can include sequences designed to have desired parameters.

The term "viable" as used herein in relation to a gene is used to refer a gene that retains its ability to encode a reference polypeptide capable of performing its normal biological function. For example, in some embodiments, a viable gene encoding an EvpB protein retains its ability to encode an EvpB protein capable facilitating *Edwardsiella ictaluri* virulence. In this regard, it is noted that the evpB gene comprises not only the coding sequence encoding the EvpB protein, but also regulatory sequences, such as the promoter. The gene also comprises sites essential for correct translation of the evpB mRNA, such as the ribosome binding site. As such, the presently-disclosed subject matter is inclusive of not only mutations in the coding regions of the evpB gene, but also mutations in those evpB gene sequences essential for correct transcription and translation of the evpB gene into a functional protein.

With respect to the EvpB protein, the phrase "functional EvpB protein," as used herein, is understood to mean a protein capable of performing the biological function of the wild-type EvpB protein. Thus, an EvpB protein that is defective in at least one of the functions of a wild-type EvpB protein is considered to be a non-functional EvpB protein.

The terms "polypeptide", "protein", and "peptide" which are used interchangeably herein, refer to a polymer of the 20 protein amino acids, or amino acid analogs, regardless of its size or function. Although "protein" is often used in reference to relatively large polypeptides, and "peptide" is often used in reference to small polypeptides, usage of these terms in the art overlaps and varies. The term "polypeptide" as used herein refers to peptides, polypeptides, and proteins, unless otherwise noted. The terms "protein", "polypeptide" and "peptide" are used interchangeably herein when referring to a gene product. Thus, exemplary polypeptides include gene products, naturally occurring proteins, homologs, orthologs, paralogs, fragments and other equivalents, variants, and analogs of the foregoing.

In some embodiments of the presently-disclosed subject matter, a live attenuated *Edwardsiella ictaluri* bacterium is provided that does not include a functional EvpB protein due to a mutation in the evpB gene. As used herein, the term "mutation" or "mutant" carries its traditional connotation and means a change or modification, inherited or introduced, in a nucleic acid or polypeptide sequence, and is used in its sense as generally known to those of skill in the art. As would be recognized by those in the art, such a change or modification can include deletions, insertions, and replacements of amino acids and nucleotides, respectively.

In some embodiments, the live attenuated bacterium contains a mutant evpB gene. In some embodiments, the mutation can be an insertion, a deletion, a substitution, or a combination thereof, provided that the mutation leads to a non-functional EvpB protein. In some embodiments, the mutation in the evpB gene is an insertion and/or a deletion mutation. In some embodiments, the mutation in the evpB gene is an in-frame deletion.

As used herein, "insertion" when referring to a nucleic acid molecule or polypeptide, describes the inclusion of one or more additional nucleotides in the nucleic acid molecule or one or more amino acids in the polypeptide, within a target, native, wild-type or other related sequence. Thus, a nucleic acid molecule that contains one or more insertions compared to a wild-type sequence, contains one or more additional nucleotides within the linear length of the sequence.

As used herein, "deletion," when referring to a nucleic acid molecule or polypeptide, refers to the deletion of one or more nucleotides from the nucleic acid molecule or deletion of one or more amino acids from the polypeptide compared to a sequence, such as a target polynucleotide or polypeptide or a native or wild-type sequence. In this regard, an "in-frame" deletion refers to a deletion that deletes a number of DNA bases that is divisible by three such that the deletion entirely removes one or more codons from the gene and, consequently, lead to the deletion of one or more amino acids from the protein.

In some embodiments, very small deletions such a stretches of at least one single base pairs can render evpB non-functional. In some embodiments, as a result of a deletion or insertion, the other base pairs are no longer in the correct reading frame. In some embodiments, each deletion or insertion of a number of base pairs indivisible by three causes such a frame shift. In some embodiments, a longer stretch of nucleotide acid of 100 base pairs or more is removed. In some embodiments, the whole evpB gene is deleted.

All techniques for the construction of non-functional mutants are well-known standard techniques including, but not limited to, amplification of the upstream and downstream regions of evpB gene by PCR, modification of the gene sequence by splicing overlap extension PCR, restriction enzyme digestion, ligation of the modified evpB gene in a suicide plasmid, and replacement of the wild-type evpB gene with the mutant gene (e.g., allelic exchange or allelic replacement). Standard recombinant DNA techniques such as amplification of the upstream and downstream regions of evpB gene by PCR, modification of the gene sequence by splicing overlap extension PCR, restriction enzyme digestion, ligation, and homologous recombination in the host strain, are all known in the art and are described, for example, in Maniatis/Sambrook (Sambrook, J. et al. Molecular Cloning: A Laboratory Manual. ISBN 0-87969-309-6). In this regard, while certain embodiments of the presently-disclosed subject matter are directed to *Edwardsiella ictaluri* bacterium, the presently-disclosed subject matter is also inclusive of additional modified bacterial strains lacking a viable gene encoding a functional EvpB protein. (e.g., other bacterium including an insertion and/or a deletion mutation in the evpB gene).

Further provided in some embodiments of the presently-disclosed subject matter, is a vaccine for protecting fish against *Edwardsiella ictaluri* infection. In some embodiments, the vaccine includes an immunogenically-effective amount of an attenuated *Edwardsiella ictaluri* bacterium described herein. In some embodiments, the fish is a catfish, such as, in some embodiments, a catfish fingerling or a catfish fry. In some embodiments, the vaccine induces a highly effective type of immune response, where, once the animal host has been vaccinated, the entry of a microbial pathogen into the host induces an accelerated recall of earlier, cell-mediated or humoral immunity which is able to control further growth of the organism before the infection can assume clinically significant proportions.

The presently-disclosed subject matter, in some embodiments, is further inclusive of composition that includes a live attenuated *Edwardsiella ictaluri* bacterium where, in some embodiments, the bacterium lacks a viable gene encoding a functional EvpB protein. In some embodiments, the composition includes an amount of the bacterium sufficient for protecting fish against infection from virulent *Edwardsiella ictaluri*. In some embodiments, in addition to an effective amount of the attenuated bacterium described above, the composition according to the present invention also contains a pharmaceutically-acceptable vehicle, carrier, or excipient. In this regard, in some embodiments, the composition is formulated for delivery to fish by immersion, injection, oral delivery, or combinations thereof.

In some embodiments, the composition may be formulated in a pharmaceutically acceptable carrier such as water, physiological saline, mineral oil, vegetable oils, aqueous sodium carboxymethyl cellulose, or aqueous polyvinylpyrrolidone. In addition, in some embodiments, the composition can also contain optional adjuvants or other pharmaceutically active agents as are conventional in the art. Without being limited thereto, suitable adjuvants include but are not limited to mineral oil, vegetable oils, alum, and Freund's incomplete adjuvant. Still other preferred adjuvants include microparticles or beads of biocompatible matrix materials, which can be comprised of any biocompatible matrix materials as are conventional in the art, including but not limited to, agar and polyacrylate. The practitioner skilled in the art will recognize that other pharmaceutically acceptable vehicle, carriers, or excipients may be used as well. For example, other adjuvants which may be used are described by Webb and Winkelstein (In: *Basic & Clinical Immunology,* 1984. Stites et al. (Eds.), Fifth Edition, Lange Medical Publications, Los Altos, Calif., pages 282-285), the contents of which are incorporated by reference herein.

Further provided, in the presently-disclosed subject matter, is a method for protecting fish against infection from virulent *Edwardsiella ictaluri*. In some embodiments, a method of protecting fish is provided that includes administering to a fish a therapeutically-effective amount of an attenuated *Edwardsiella ictaluri* bacterium lacking a viable gene encoding a functional EvpB protein. In some embodiments, the administering is selected from a group consisting of immersion, injection, oral delivery, and a combination thereof. In some embodiments, the fish is a catfish. In some embodiments, the catfish is fry. In some embodiments, the catfish is a fingerling. In some embodiments, the bacterium is mixed with a fish feed to form a fish feed mixture and the fish feed mixture is then delivered to the fish for oral consumption.

The compositions and/or bacterium of the presently-disclosed subject matter can be administered to the subject animal by any convenient route which enables the bacterium to elicit an immune response, including, but not limited to, intraperitoneal or intramuscular injection, bath immersion, oral administration, or nasal administration. In some embodiments, administering the composition by immersion immunization offers low cost per fish immunized, mass immunization of large numbers of fish, reduced stress, significantly higher rates of fish survival and the absence of adverse reactions to vaccination. Furthermore, immersion vaccination is an effective method for mass vaccination of smaller fish that cannot be injected or subjected to skin punctures.

Under current catfish production practices, there is about two weeks post-hatch available for vaccinating fry by immersion before the fry are stocked into nursery ponds. As such, in some embodiments, the live attenuated bacteria are administered to the catfish during this period by immersion. Once fish are stocked into nursery and grow-out ponds, oral delivery can then be used for vaccination. Accordingly, in some embodiments, the live attenuated bacteria are administered to the catfish by oral administration.

With further respect to the administration of a bacterium described herein, the bacterium can be administered in a single dose or in a plurality of doses. In some embodiments, dependent upon rearing conditions, the vaccine may be administered in multiple doses, the timing of which may be readily determined by the skilled artisan.

Regardless of the particular mode and timing of administration used in accordance with the methods of the presently-disclosed subject matter, the bacterium, including the bacterium-based compositions and vaccines described herein, are typically administered in an amount effective to achieve the desired response (i.e., protection against *Edwardsiella ictaluri*). As such, the term "effective amount" is used herein to refer to an amount of the therapeutic composition (e.g., a vaccine or other composition including a live attenuated bacterium of the presently-disclosed subject matter) sufficient to produce a measurable biological response (e.g., an immune response against *Edwardsiella ictaluri* infection). In this regard, in some embodiments, the term "therapeutically effective" is used interchangeably herein with the phrase "immunogenically effective" to refer to an amount of live attenuated *Edwardsiella ictaluri* bacteria of the presently-disclosed subject matter sufficient to induce an effective immune response in a host against a virulent *Edwardsiella ictaluri* bacterium. Actual dosage levels of active ingredients in a therapeutic composition of the presently-disclosed subject matter (e.g., the bacterium) can be varied so as to administer an amount of a composition that is effective to achieve the desired therapeutic response for a particular subject and/or application. Of course, the selected dosage level and amount of the bacterium and the other components of such a composition will depend upon a variety of factors including the activity of the bacterium, formulation, the route of administration, combination with other drugs or treatments, severity of the condition being treated, and the physical condition and prior medical history of the subject being treated. Preferably, a minimal dose is administered, and dose is escalated in the absence of dose-limiting toxicity to a minimally effective amount. Determination and adjustment of a therapeutically effective dose, as well as evaluation of when and how to make such adjustments, are known to those of ordinary skill in the art. In some embodiments, the amount of the live *Edwardsiella ictaluri* bacteria administered to a subject (e.g., a catfish)

ranges from about $10^5$ to about $10^9$ CFU/ml water when administering by immersion. In some embodiments, the dose is about $10^7$ to about $10^9$ CFU/ml water. Preferably, the dose is about $10^8$ to about $10^9$ CFU/ml water.

The presently-disclosed subject matter is further illustrated by the following specific but non-limiting examples. The following examples may include compilations of data that are representative of data gathered at various times during the course of development and experimentation related to the present disclosure.

EXAMPLES

Materials and Methods for Examples 1-6

Bacterial strains, plasmids, and growth conditions. Bacterial strains and plasmids utilized are listed in Table 1. *Edwardsiella ictaluri* 93-146 wild type (WT) strain was cultured in brain heart infusion (BHI) agar or broth (Difco, Sparks, Md.) and incubated at 30° C. throughout the study. *E. coli* CC118λpir and SM10λpir strains were cultured on Luria-Bertani (LB) agar or broth (Difco) and incubated at 37° C. throughout the study. When required, media were supplemented with the following antibiotics and reagents: ampicillin (Amp: 100 mg/ml), colistin sulfate (Col: 12.5 mg/ml), sucrose (5%), and/or mannitol (0.35%) (Sigma-Aldrich, Saint Louis, Mo.).

TABLE 1

Bacterial strains and plasmids

| Bacterial strain | Strains | Reference |
|---|---|---|
| *Edwardsiella ictaluri* | | |
| 93-146 | Wild type; pEI1$^+$; pEI2$^+$; Col$^r$ | (Lawrence et al., 1997) |
| EiΔevpB | 93-146 derivative; pEI1$^+$; pEI2$^+$; Col$^r$ | This study |
| *Escherichia coli* | | |
| CC118λpir | Δ(ara-leu); araD; ΔlacX74; galE; galK; phoA20; thi-1; rpsE; rpoB; argE(Am); recA1; λpirR6K | (Herrero et al., 1990) |
| SM10λpir | thi; thr; leu; tonA; lacY; supE; recA; ::RP4-2-Tc::Mu; Kmr; λpirR6K | (Miller and Mekalanos, 1988) |
| Plasmids | | |
| pMEG-375 | 8142 bp, Amp$^r$, Cm$^r$, lacZ, R6K ori, mob incP, sacR sacB | (Dozois et al., 2003) |
| pEiΔevpB | 10507 bp, pMEG-375, ::ΔevpB | This study |

Sequence analysis. The nucleotide sequences of the T6SS operon were obtained from the *Edwardsiella ictaluri* 93-146 genome located in the National Center for Biotechnology Information (NCBI) (GenBank accession: CP001600) (Williams et al., 2012). The Basic Local Alignment Search Tool (BLAST) was used to determine the sequence of evpB open reading frame and adjacent sequences.

Construction of EiΔevpB in-frame deletion mutant. The in-frame deletion of the *Edwardsiella ictaluri* evpB gene (NT01EI_2738) was constructed by allelic exchange as described previously (Abdelhamed et al., 2013). Briefly, 1,210 bp upstream and 1,155 bp downstream regions of evpB were amplified from *Edwardsiella ictaluri* 93-146 genomic DNA with A/B and C/D primer pairs (Table 2), respectively. These PCR products were diluted and used as template in a splicing overlap extension PCR (Horton et al., 1990) with the A/D primers to generate (2,365 bp) ΔevpB deletion fragment. The resulting ΔevpB deletion fragment was purified using a QIAQUICK PCR Purification Kit (QIAGEN, Valencia, Calif.), digested with XbaI restriction enzyme, and ligated into pMEG-375, which is pre-digested with the same enzyme and dephosphorylated. Then, the ligation product was transformed into *E. coli* CC118λpir competent cells and transformants were selected on LB plates containing Amp. The resulting colonies were screened by colony PCR and confirmed further by restriction digestion and sequencing.

TABLE 2

Primers used to generate and verify in-frame deletion of the *Edwardsiella ictaluri* evpB gene.

| Primers | Sequence | RE$^a$ |
|---|---|---|
| EiEvpBF01 | A AATCTAGAGGACGACTCACCTCCGTTATC SEQ ID NO. 1 | XbaI |
| EiEvpBR189 | B TACGTCACCGGAAACTGTCAC SEQ ID NO. 2 | |
| EiEvpBF1375 | C GTGACAGTTTCCGGTGACGTAGATGTCAGC GATATTCCAGGT SEQ ID NO. 3 | |
| EiEvpBR01 | D AATCTAGAGTTGATCGCTGTACCGATGTC SEQ ID NO. 4 | XbaI |
| EiEvpB_Seq | GCTTCCCAAGCTGAAAGAAC SEQ ID NO. 5 | |

$^a$RE stands for restriction enzyme added to the 5'-end of the primer sequence.
$^b$Bold letters at the 5'-end of the primer sequence represent RE site added. AA nucleotides were added to the end of each primer containing a RE site to increase the efficiency of enzyme cut. Underlined bases in primer C indicate reverse complemented primer B sequence.

The plasmid pEiΔevpB was transformed into SM10λpir, which is used as donor in conjugation to allow transfer of the pEiΔevpB into with *Edwardsiella ictaluri* for allelic exchange to occur. Transformants were selected on BHI agar containing Amp and Col at 30° C. for 2 days. To allow the second homologous recombination, a single Amp resistant merodiplod colony was plated on BHI agar and incubated at 30° C. for 2 days. Loss of the suicide vector was carried out by plating overnight cultures onto LB agar, with 5% sucrose and 0.35% mannitol, and incubating plates maintained at 28° C. for 3 days. Amp-sensitive colonies were screened by colony PCR using the A/D primers to identify the desired mutation, which was further confirmed by sequencing.

Determination of safety and efficacy of EiΔevpB in catfish fingerlings.

The virulence and efficacy of the EiΔevpB strain was performed, as described in earlier work (Abdelhamed et al., 2013). Briefly, 240 specific-pathogen-free (SPF) channel catfish fingerlings (13.88±0.27 cm, 27.77±1.04 g) were stocked at a rate of 20 fish per tank in 40 liter tanks supplied with flow-through, dechlorinated water with constant aeration and allowed to acclimate for one week. The tanks were divided into three groups of four replicates. The three groups were EiΔevpB, EiWT (positive control; i.e., *Edwardsiella ictaluri* wild-type), and BHI (negative/sham control). The fish were then challenged by immersion for 1 h in water containing approximately $3.32 \times 10^7$ CFU/ml water and then flow-through conditions were resumed. During the experiments, the fish were observed daily and mortalities were recorded. The water temperature was maintained at 26±2° C. during the course of the experiment. At 21-days post-immunization, the vaccinated fish were re-challenged with *Edwardsiella ictaluri* WT by immersion for 1 h in water containing approximately ($3.83 \times 10^7$ CFU/ml water), as described above. Fish mortality was recorded daily for 14 days.

Determination of safety and efficacy of EiΔevpB in catfish fry. Nine hundred 14 day old SPF channel catfish fry were stocked in 18 tanks (approximately 50 fry/tank). Tanks were randomly assigned into six treatment groups with three replicates per group. Treatment groups consisted of high ($3.32 \times 10^7$ CFU/ml water) and low ($3.32 \times 10^6$ CFU/ml water) doses of EiΔevpB, EiWT (positive control), and BHI (negative/sham control). Immersion challenge was conducted same as fingerling challenge described above. At 21 days post-vaccination, fry were infected with *Edwardsiella ictaluri* WT by immersion exposure at approximately $3.10 \times 10^7$ CFU/ml water. Fish mortality was recorded for 14 days.

Determination of the optimal vaccine dose of EiΔevpB in catfish fry. To determine the optimal dose, 7-day post-hatch fry were challenged with three different doses of EiΔevpB strain and fry mortality was recorded for 30 days. Survived fry were challenged by *Edwardsiella ictaluri* WT. Briefly, approximately 750 fry were stocked into 15 tanks (50 fry/tank). The tanks were divided into five groups with three replicates per group. Treatments groups consisted of three doses of EiΔevpB ($3.72 \times 10^6$, $3.72 \times 10^7$, and $3.72 \times 10^8$ CFU/ml water), BHI (negative/sham control), and EiWT (positive control). Fish were monitored daily and dead fry were removed and recorded from each tank. After 30 days post vaccination, fish were infected with the *Edwardsiella ictaluri* WT by immersion in water ($3.80 \times 10^7$ CFU/ml water) for 1 h. Fish mortality was recorded daily for 21 days.

Comparison of EiΔevpB and commercial vaccine AQUA-VAC-ESC in catfish fingerlings. Virulence and efficacy of EiΔevpB strain were compared with AQUAVAC-ESC in catfish fingerlings. Approximately 320 channel catfish fingerlings were stocked into 16 tanks at a rate of 20 fish/tank. Each treatment had four replicate tanks. Treatments consisted of AQUAVAC-ESC, EiΔevpB strain, *Edwardsiella ictaluri* WT (positive control), and BHI (negative/sham control). The fingerlings were vaccinated by immersion in water containing approximately $3.72 \times 10^7$ CFU/ml for 1 h. Fish were monitored and dead fish were removed daily. After 21 days, immunized fish were infected with *Edwardsiella ictaluri* WT by immersion in water with $3.80 \times 10^7$ CFU/ml for 1 h. Mortality was recorded for 21 days.

Comparison of EiΔevpB and commercial vaccine AQUA-VAC-ESC in catfish fry. Virulence and efficacy of EiΔevpB strain were compared with AQUAVAC-ESC in two-week old catfish fry. Approximately 800 channel catfish fry were stocked into 16 tanks at a rate of 50 fish/tank. Each treatment had four replicate tanks. Treatments consisted of EiΔevpB strain, AQUAVAC-ESC, *Edwardsiella ictaluri* WT (positive control), and BHI (negative/sham control). The fry were vaccinated by immersion in water containing approximately $1 \times 10^7$ CFU/ml for 1 h. Fish were monitored and dead fish were removed daily. After 21 days, immunized fish were infected with *Edwardsiella ictaluri* WT by immersion in water with $2.08 \times 10^7$ CFU/ml for 1 h. Mortality was recorded for 21 days.

Statistical analysis. Survival data were analyzed using Kaplan-Meier Log Rank Survival Analysis, and Holm-Sidak method will be used for pairwise comparisons.

Example 1

T6SS in *Edwardsiella ictaluri* Genome

Analysis of the published *Edwardsiella ictaluri* genome revealed the presence of 16 genes of T6SS (evpP, plus genes from NT01E1_2737 to NT01E1_2751), which encode for the T6SS apparatus, chaperones, effectors, and regulators (FIG. 1). The entire operon size was 20,724 bp.

Example 2

Construction of the EiΔevpB Mutant

An in-frame deletion was successfully introduced to the evpB gene in the *Edwardsiella ictaluri* chromosome. The resulting EiΔevpB strain contained a deletion of 1167 bp out of 1488 bp open reading frame (78.42%), resulting in a 389 amino acids loss from the *Edwardsiella ictaluri* evpB gene. This in-frame deletion was verified by PCR and sequencing of the amplified evpB fragment from the EiΔevpB mutant verified the loss of 1167 bp from evpB.

Example 3

Virulence and Efficacy of EiΔevpB in Catfish Fingerlings

Figure 2A:
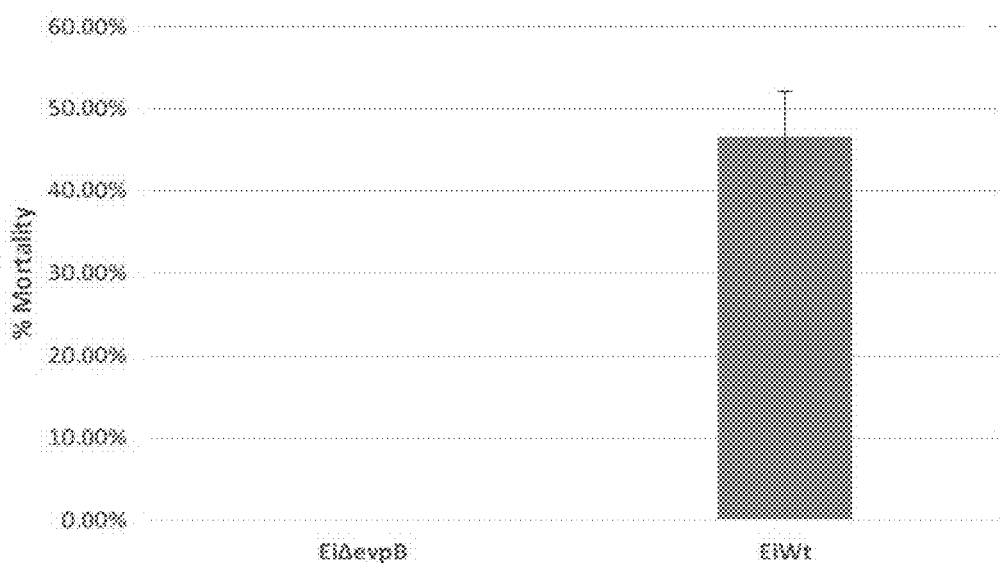
FIGS. 2A & 2B include bar graphs showing the results of virulence (FIG. 2A) and efficacy (FIG. 2B) trials of EiΔevpB in catfish fingerlings.
Figure 2B:
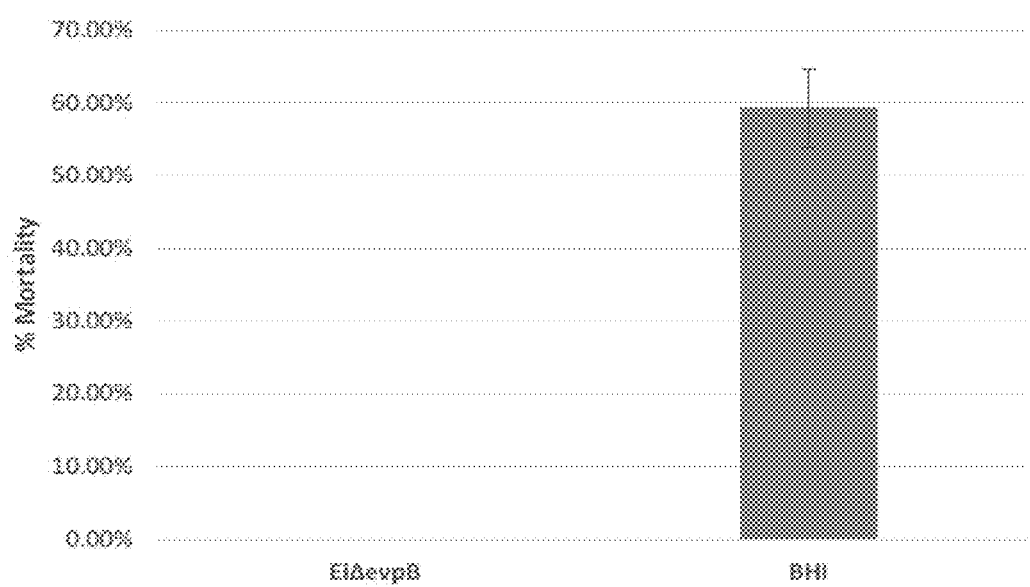

The virulence of EiΔevpB was evaluated in catfish fingerlings. Results indicated EiΔevpB was fully attenuated (0% fish mortality) compared to *Edwardsiella ictaluri* WT (46.91% fish mortality) (FIG. 2A). Evaluation of the efficacy at 21 days post-vaccination with EiΔevpB strain indicated complete protection (0% fish mortality), whereas sham group (BHI added fish) showed 59.31% mortality (FIG. 2B).

Example 4

Virulence and Efficacy of EiΔevpB in Fry

Figure 3A:
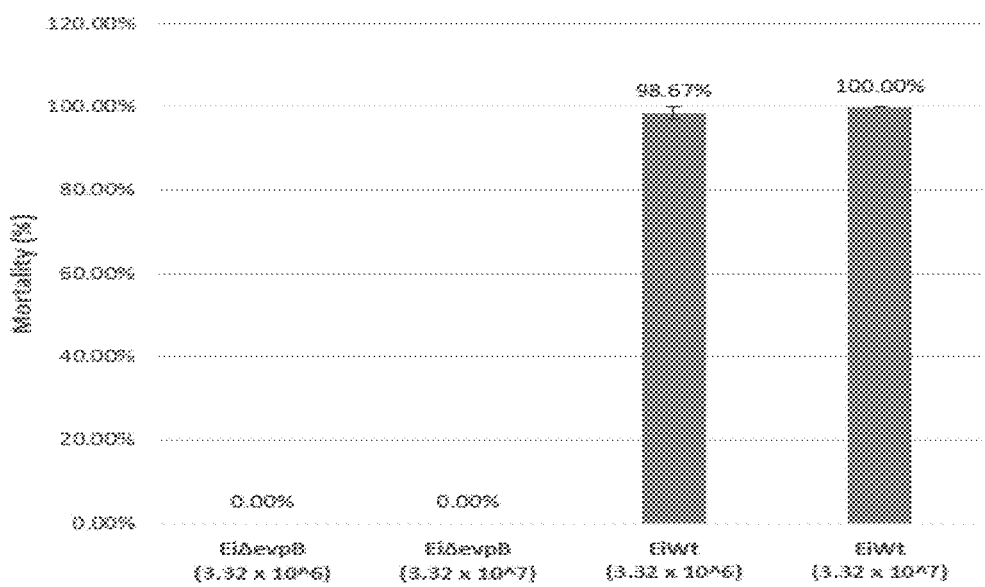
FIGS. 3A & 3B include bar graphs showing the results of virulence (FIG. 3A) and efficacy (FIG. 3B) trials of EiΔevpB in catfish fry.
Figure 3B:
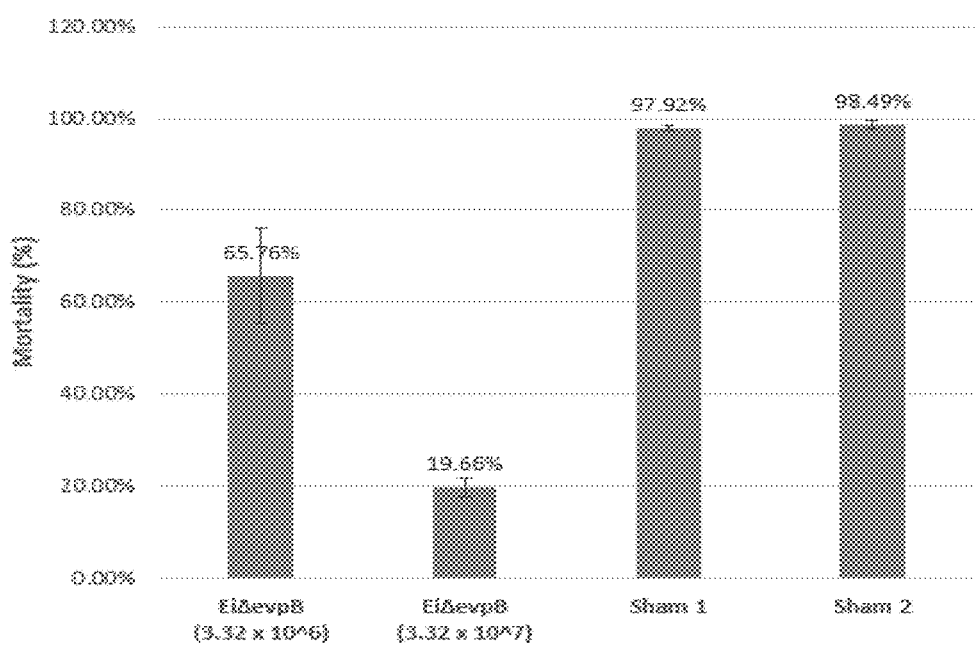

The EiΔevpB strain was evaluated in two-week old catfish fry by immersion. EiΔevpB was attenuated completely in fry at two doses ($3.32 \times 10^6$ and $3.32 \times 10^7$). In contrast, 98.67% and 100% of the fry exposed to *Edwardsiella ictaluri* WT died (FIG. 3A). The fry vaccinated with low and high doses ($3.32 \times 10^6$ and $3.32 \times 10^7$) of EiΔevpB showed 65.76% and 19.66% mortalities when challenged with *Edwardsiella ictaluri* WT (approximately $3.10 \times 10^7$ CFU/ml water) 21 days post-vaccination. On the contrary, sham vaccinated groups showed very high mortalities (97.92% and 98.49%) when challenged with the same dose of *Edwardsiella ictaluri* WT (FIG. 3B).

Example 5

Optimal Vaccine Dose of EiΔevpB in Catfish Fry

Figure 4A:
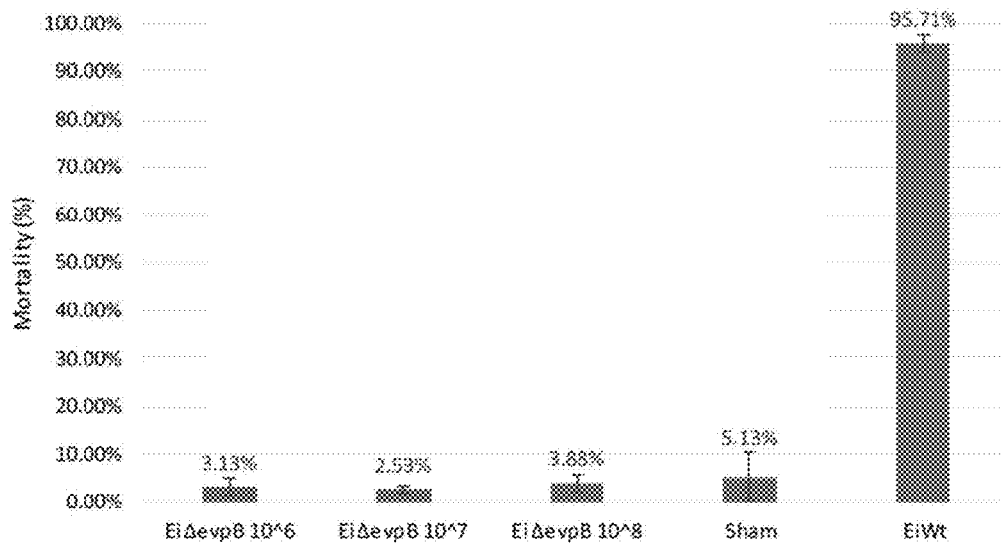
FIGS. 4A & 4B include bar graphs showing the results of virulence (FIG. 4A) and efficacy (FIG. 4B) trials of different vaccination doses of EiΔevpB in catfish fry.
Figure 4B:
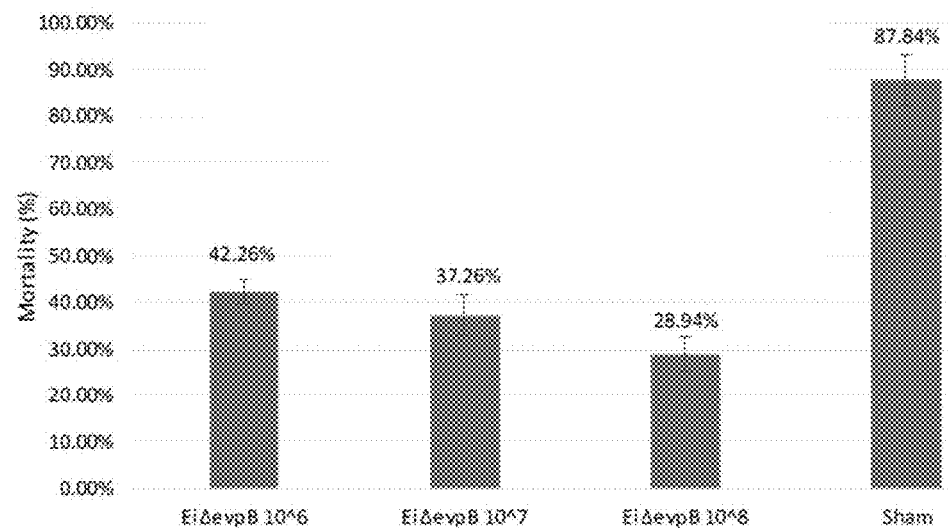

Mortalities when fry vaccinated with increasing doses of EiΔevpB ($3.72 \times 10^6$, $3.72 \times 10^7$, and $3.72 \times 10^8$ CFU/ml water) were 3.13%, 2.53%, and 3.88%, respectively, while mortalities in the negative/sham (BHI) and positive (EiWT) controls were 5.13% and 95.71%, respectively (FIG. 4A). After 30 days post-vaccination, vaccinated fry were challenged with *Edwardsiella ictaluri* WT to determine protection from increasing doses of EiΔevpB vaccination. The percent mortality in the fry vaccinated at doses of $3.72 \times 10^6$, $3.72 \times 10^7$, and $3.72 \times 10^8$ CFU/ml water were 42.26%, 37.26%, and 28.94%, respectively, which were significantly lower ($p<0.05$) than the sham-vaccinated fry (87.84% mortality) (FIG. 4B).

Example 6

Figure 5A:
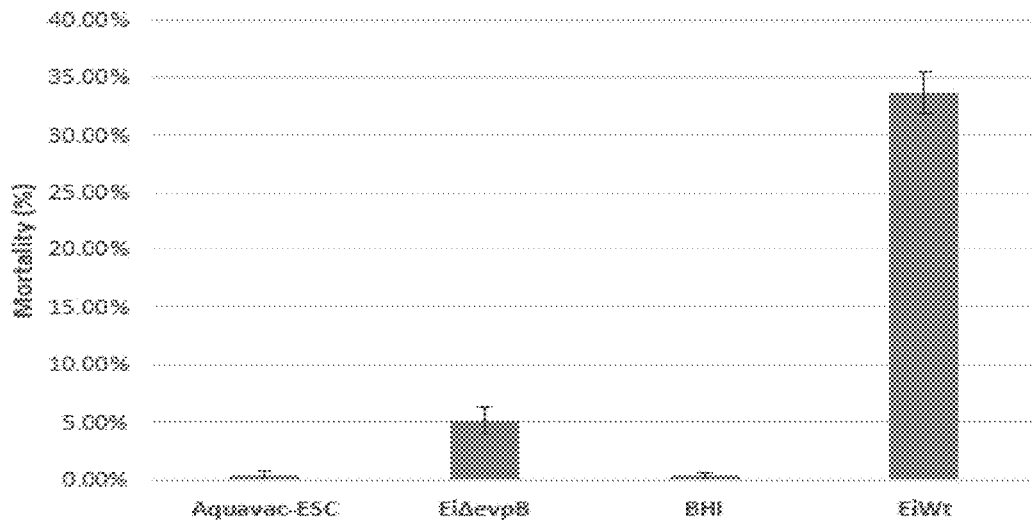
FIGS. 5A & 5B include bar graphs showing the results of virulence (FIG. 5A) and efficacy (FIG. 5B) trials of EiΔevpB and AQUAVAC-ESC in catfish fingerlings.
Figure 5B:
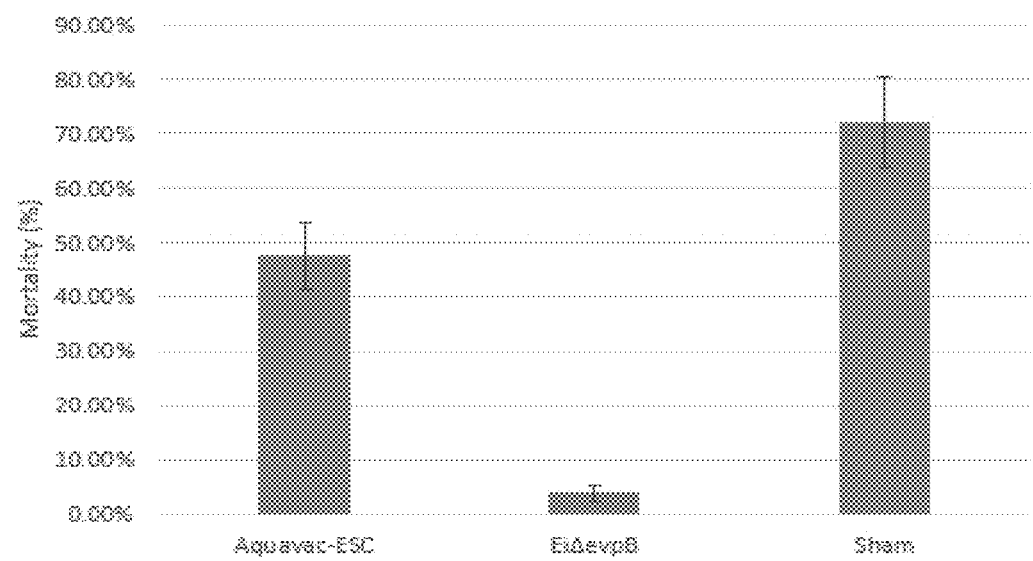

Comparison of EiΔevpB to Commercial Vaccine AQUAVAC-ESC in Catfish Fingerlings Comparison of EiΔevpB and AQUAVAC-ESC in fingerling catfish showed very low mortalities for both strains (5.14% and 0.38%, respectively) (FIG. 5A). When vaccinated fingerlings challenged with *Edwardsiella ictaluri* WT, EiΔevpB strain elicited significantly higher protection (3.80% mortality) compared to AQUAVAC-ESC (47.52% mortality) (FIG. 5B).

Example 7

Comparison of EiΔevpB to Commercial Vaccine AQUAVAC-ESC in Catfish Fry

Figure 6A:
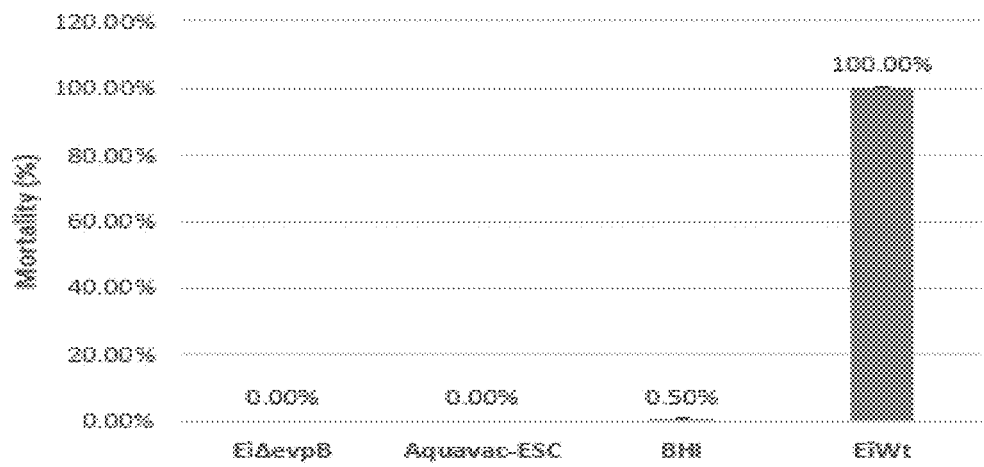
FIGS. 6A & 6B include bar graphs showing the results of virulence (FIG. 6A) and efficacy (FIG. 6B) trials of EiΔevpB and AQUAVAC-ESC in catfish fry.
Figure 6B:
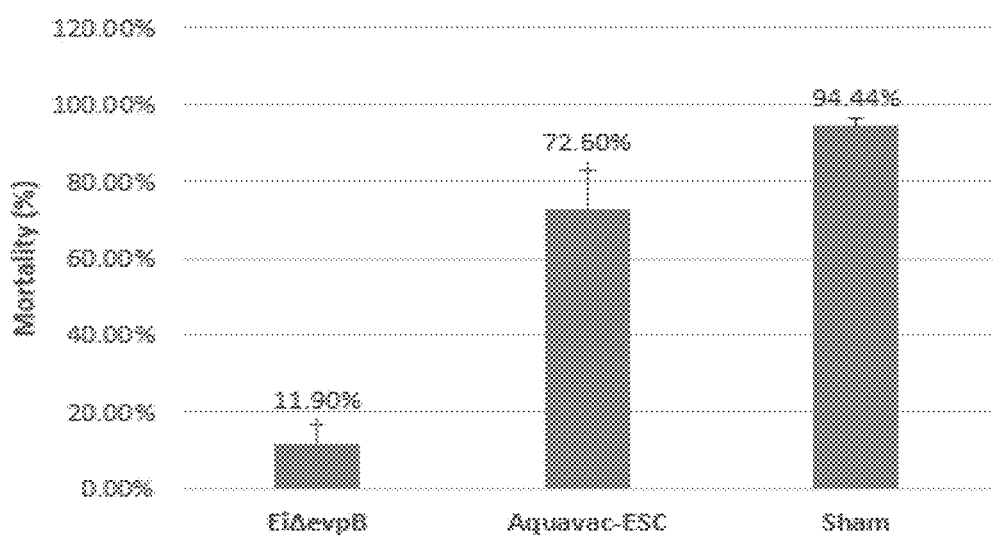

Comparison of EiΔevpB and AQUAVAC-ESC in fry catfish showed no mortalities for both strains (FIG. 6A). When vaccinated fry challenged with *Edwardsiella ictaluri* WT, EiΔevpB strain elicited more than six fold better protection (11.90% mortality) compared to AQUAVAC-ESC (72.60% mortality) (FIG. 6B).

Discussion of Examples 1-7

The foregoing studies describe the development of a live attenuated *Edwardsiella ictaluri* vaccine strain based on a mutation in the evpB gene, which is the second gene located on the T6SS operon. The first step was the construction of the EiΔevpB strain by in-frame deletion of the evpB gene leaving 189 bp at the 5' end and 132 bp at the 3' end. The EiΔevpB strain was nonpolar and did not affect expression of the downstream genes of the operon. Further, the EiΔevpB strain did not contain any selection antibiotics and thus it was safe for the environment. Presence of extraneous antibiotic resistance is generally regarded as not desirable in vaccine strains to avoid spreading of antibiotic resistance genes. The *Edwardsiella ictaluri* EvpB protein was previously annotated as eip55 (Moore et al., 2002) but it was not known that eip55 was part of the T6SS. The eip55 is expressed during *Edwardsiella ictaluri* infection and antigenic to channel catfish. The percent sequence identity at the amino acid level between *Edwardsiella ictaluri* and *E. tarda* EvpBs (Srinivasa Rao et al., 2004) was high (96.5%).

The EiΔevpB strain reported in the foregoing studies was completely attenuated in catfish fingerlings. Moreover, vaccination of fingerlings with EiΔevpB provided complete protection against subsequent challenge with the *Edwardsiella ictaluri* WT 21 days post-vaccination. Safe and protective live attenuated vaccines are desirable in commercial catfish vaccination. The foregoing studies showed that the attenuation of the EiΔevpB strain was capable of being used as a live attenuated vaccine for catfish fingerlings.

In further experiments described above, two-week old catfish fry vaccinated with EiΔevpB strain at sub-vaccination and vaccination doses demonstrated that the EiΔevpB strain was attenuated completely in channel catfish fry at both doses. *Edwardsiella ictaluri* WT challenge of the vaccinated fry showed better protection when higher vaccination doses were used, which indicated that vaccine efficacy appeared to be dependent on exposure dose. To further test that observation, fry were vaccinated with increasing doses of EiΔevpB. It was determined that the vaccine dose of $10^8$ CFU/ml water elicited low-level mortality and demonstrated the highest protection against *Edwardsiella ictaluri* WT. The vaccine doses of $10^6$ and $10^7$ CFU/ml water were also safer but data indicated less protection than the highest vaccination dose ($10^8$ CFU/ml water).

A comparison study using immersion vaccination was also conducted to compare the efficacy of EiΔevpB to the commercially available vaccine (AQUAVAC-ESC) in channel catfish fingerlings and in channel catfish fry. In both trials, the vaccine strain EiΔevpB provided better (more than twelve-fold and six-fold, respectively) protection than AQUAVAC-ESC.

The results from fry and fingerling experiments showed that evpB is important in *Edwardsiella ictaluri* virulence, which is consistent with findings in *E. tarda* PPD130/91, where a deletion of evpB led to reduced virulence in blue gourami and impaired replication in gourami phagocytes (Srinivasa Rao et al., 2004).

Several T6SS proteins are important for bacterial pathogenesis. However, the function of most T6SS proteins remains unknown (Filloux et al., 2008; Silverman et al., 2012). This is the first report that evpB is required for *Edwardsiella ictaluri* virulence. This is also the first study that linked T6SS and virulence in *Edwardsiella ictaluri*. The results shown here suggest that deletion of evpB gene provides an excellent live attenuated vaccine candidate.

Live attenuated bacterial vaccines activate immune responses by mimicking the route of natural infection, possess intrinsic adjuvant properties, and can be administrated as mucosal vaccines. In this regard, a consideration for the success of vaccination in catfish fry (14 d post-hatch) is that the immune system may not be fully developed, and live attenuated vaccines must achieve a balance between lack of pathogenicity and sufficient immunogenicity to provide protective immunity. Currently available vaccines do not exhibit this balance. As with most fish, the adaptive immune system is poorly developed in early developmental stages of fish, at least with respect to humoral immunity (Ellis 1988). Therefore, it has been speculated that hatchery fry may not be able to effectively respond to vaccination. Despite this, the foregoing results showed that vaccination of two-week old catfish fry with attenuated EiΔevpB strain provided protective immunity against subsequent *Edwardsiella ictaluri* WT challenge. It is important to bear in mind that the protective immunity in channel catfish against ESC is determined by cellular immune mechanisms (Shoemaker et al., 1997; Thune et al., 1997) which generally precedes the development of humoral immunity. Although it is uncertain when cellular immunity is functional in channel catfish, the cellular immune response in trout has been shown to be functional at 14 d of age (Tatner and Manning, 1985).

In conclusion, the EiΔevpB described here offers a number of advantages and meets several criteria important for use as a live attenuated vaccine against ESC. First, EiΔevpB is safe and does not cause or causes only minimal mortality in fingerlings and fly. Second, vaccination of fingerlings with EiΔevpB provides complete protection and vaccination of fry resulted about 80% protection against subsequent challenge with *Edwardsiella ictaluri* WT. Third, EiΔevpB is well characterized genetically. Consequently, the evpB mutation renders the organism a virulent without affecting its ability to replicate in fish and produce virulence determinants, which is important for persistence of EiΔevpB in host.

Additional Studies. Additional studies were conducted in earthen ponds as follows. Five identical earthen ponds (0.12 acre, average depth of 1.5 m) located at the South Farm Aquaculture Research Facility at Mississippi State University were used. Ponds (A13, A13, A15, A2, and B3) were prepared four weeks prior to stocking. The designated ponds were filled with water and fertilized with Perfect Pond Plus Fertilizer (Alabama, USA) and dissolved oxygen was measured daily before stocking. Supplemental aeration was provided to each pond by Air-O-Lator 24 h and 7 days a week. Four square pens (4×4×4 feet) were placed in each pond representing four replicates for each treatment. The four pens in each pond were located in a square pattern around the Air-O-Lator to enhance aeration. Throughout the experiment, the ponds were managed according to industry practices. Dissolved oxygen (DO) and temperature were monitored twice daily in the morning and afternoon using a portable dissolved oxygen meter (YSI model 550A, YSI Incorporated, San Diego, Calif.) on the pond bank. Water was added to the ponds periodically to replace the lost through evaporation and seepage.

Approximately 6,000 17 day-old specific pathogen free (SPF) catfish fry were stocked into five tanks (1200/tank) supplied with flow-through dechlorinated municipal water in the College of Veterinary Medicine. Water temperature was maintained at 25-26° C. throughout these indoor conditions. The five tanks corresponded to five treatment groups [EiΔevpB immersion, EiΔevpB oral, EiΔevpB immersion-oral, AQUAVAC-ESC (commercial vaccine), and sham]. Two days later, catfish fry (19 days post-hatch) in three treatment groups (EiΔevpB immersion, EiΔevpB immersion-oral, and AQUAVAC-ESC) were immersion vaccinated indoors ($3.93 \times 10^7$ CFU/ml of water for 1 h). Fish in the sham-vaccinated group were exposed to an equivalent volume of BHI broth. Fry in all treatments were moved to the ponds on the same day in aerated containers. Each group was then stocked into four net-pens at a rate of 1200 fry/pond (300 fry/pen). The pens were covered with a lid to prevent birds and other animals from preying on the fish. Fish were fed twice a day by hand, once in the morning and afternoon, with a commercial catfish feed. Changing to a larger feed pellet was determined according to the behavior and size development of the fry in each pond. Fish were observed after feeding, and the activity of feeding was documented.

Oral vaccination. The overnight culture of EiΔevpB containing $3.52 \times 10^9$ CFU/ml was mixed with commercial feed pellets at a rate of 20% (weight to volume). The vaccine-feed was mixed by a hand mixer until all liquid was absorbed. The average amount of feed consumed one week prior to vaccination was used to estimate the amount of feed to use on vaccination days. Less than 28 days after pond stocking, oral vaccination was conducted by feeding vaccine-feed daily for five days, followed by five days feeding with no vaccine, and followed by five days feeding vaccine. The other ponds were fed similarly but without adding the vaccine to feed. The commercial vaccine strain was not included in the oral vaccination experiment because it is not licensed for oral vaccination. Following vaccination, fish were fed regular feed without adding the vaccine to feed for 21 days.

ESC Challenge. Three months after immersion vaccination (35 days following the oral vaccination), when water temperatures were conducive for *Edwardsiella ictaluri* infection (22-24° C.), fish were challenged with wild-type *Edwardsiella ictaluri* strain 93-146 in the feed (challenge feed). Overnight culture of wild-type *Edwardsiella ictaluri* containing $2.71 \times 10^9$ CFU/ml was mixed with commercial feed at a rate of 20% (weight to volume), and each pond was fed for five consecutive days with challenge feed (average feed 600 g/pond/five days) followed by a five-day break, then another five days of challenge feed.

Harvesting the ponds and measuring procedures. The study was terminated approximately five weeks later, when the water temperature was less than 18° C. Fingerling fish were collected after three months of growing in earthen ponds. At the end of the trial, fish were harvested and euthanized in water containing 300 mg/L MS-222. The total number of fish remaining and total weight in each pen was determined. Thirty individual fish, representing 10% of the initial stocking population, from each pen were selected randomly to determine the average individual weight and length. The mortality rate for each pen was determined based on initial stocking numbers and numbers of remaining fish in each pen at the end of the study.

Statistical analysis. In the field study, the effect of the different treatments on the survival of fish was assessed with mixed model logistic regression using PROC GLIMMIX in SAS for Windows 9.4 (SAS Institute, Inc., Cary, N.C., USA). The number of live fish in a replication at the end of the trial was the outcome assessed using an events/trials syntax. Treatment was the fixed effect evaluated in the model. Replication within a treatment group was included as a random effect in the model. The sham-vaccinated and AQUAVAC-ESC treatment groups were the referents for comparisons of the effect of the other treatments using an lsmestimate statement. The results of the analysis were presented as odds ratios for survival and probability of survival. The effect of the different treatments on the total weight of fish within a replication at the end of the trial was assessed by analysis of variance using PROC GLIMMIX in SAS for Windows 9.4. The results of the analysis were presented as least squares means and their standard errors. The sham-vaccinated and AQUAVAC treatment groups were the referents for comparisons of the effect of the other treatments using an lsmestimate statement adjusting the p-values for multiple comparisons with the simulate option. The effects of the different treatments on the weight and length of 30 fish within a replication at the end of the trial were assessed in separate mixed model analyses using PROC GLIMMIX in SAS for Windows 9.4. Treatment was the fixed effect assessed in each model while replication within a treatment group was included as a random effect. The results of the analysis were presented as least squares means and their standard errors. The sham-vaccinated and AQUAVAC-ESC treatment groups were the referents for comparisons of the effect of the other treatments using an lsmestimate statement adjusting the p-values for multiple comparisons with the simulate option. The distribution of the conditional residuals was evaluated for each model to determine the appropriateness of the statistical model for the data. A significance level of 0.05 was used for all analyzes.

Example 8

Figure 7:
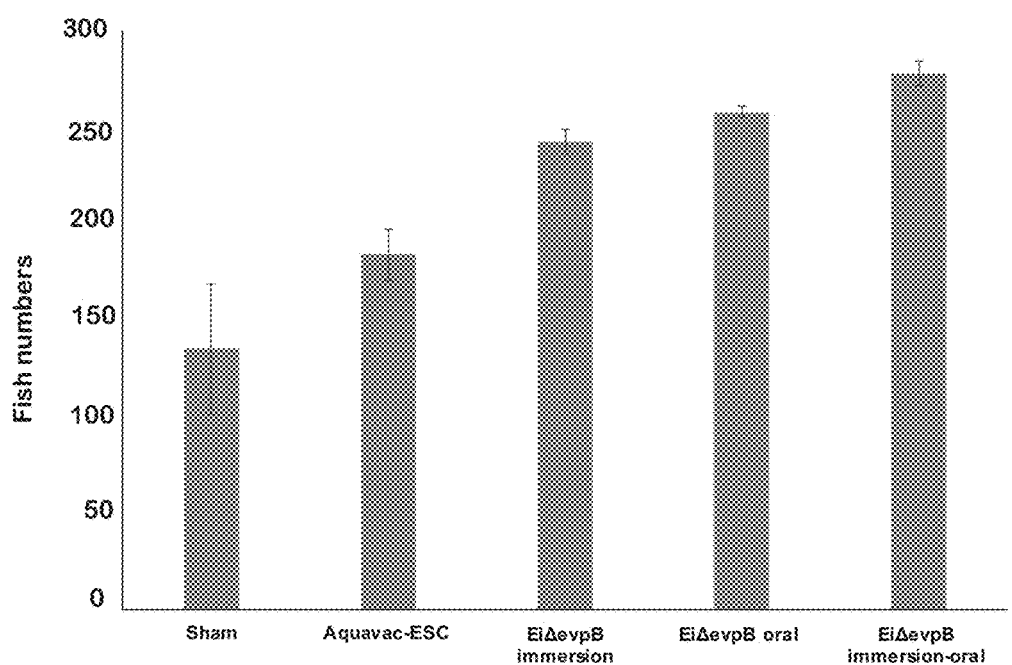
FIG. 7 is a bar graph showing the number of fish remaining in each pond at harvest. This data represents the mean of four replicate pens.

Comparison of EiΔevpB to Commercial Vaccine AQUAVAC-ESC in Catfish Fry: Fry Survival At harvest, an average of 243 fish/pen remained in the EiΔevpB immersion vaccinated pond, 258 fish/pen remained in the EiΔevpB oral vaccinated pond, and 278 fish/pen remained in the EiΔevpB immersion-oral vaccinated pond. This was significantly higher (p<0.05) from both the average of 135 fish/cage remained in the sham-vaccinated pond, and 184 fish/cage remained in the AQUAVAC-ESC vaccinated pond (FIG. 7).

Example 9

Figure 8:
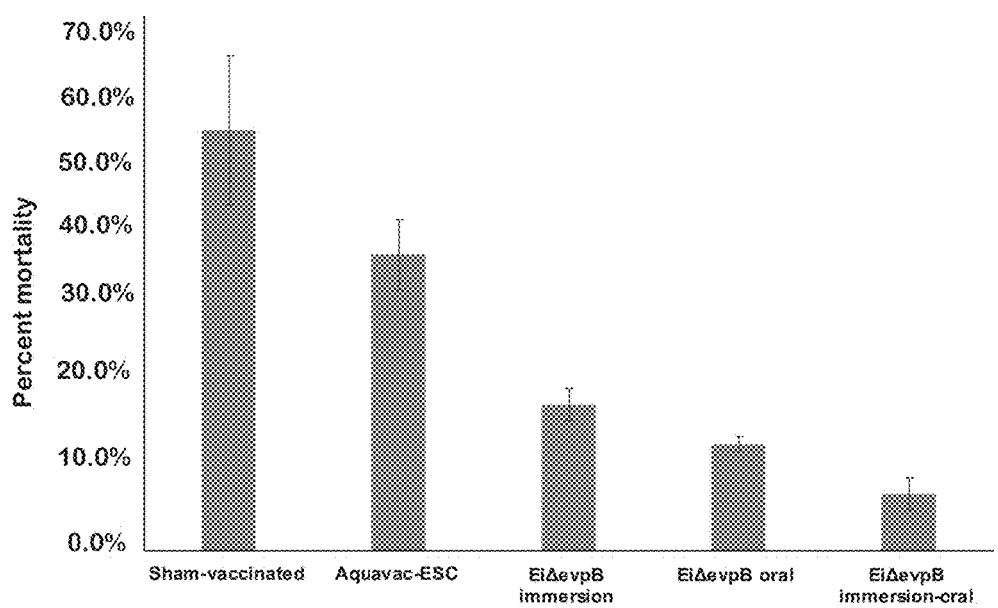
FIG. 8 is a bar graph showing the percent mortalities in each pond. The data represents the mean of four replicate pens in each pond.

Comparison of EiΔevpB to Commercial Vaccine AQUAVAC-ESC in Catfish Fry: Mortality The mean percent mortality for fish vaccinated with EiΔevpB by immersion (19.17%), oral (14%), and immersion-oral combination (7.42%) were significantly lower (p<0.05) than sham-vaccinated (55.00%) and the AQUAVAC-ESC vaccinated groups (38.75%). Conversely, there was no significant different (p>0.05) in the percent mortality between the AQUAVAC-ESC vaccinated and sham-vaccinated groups (FIG. 8).

Example 10

Figure 9:
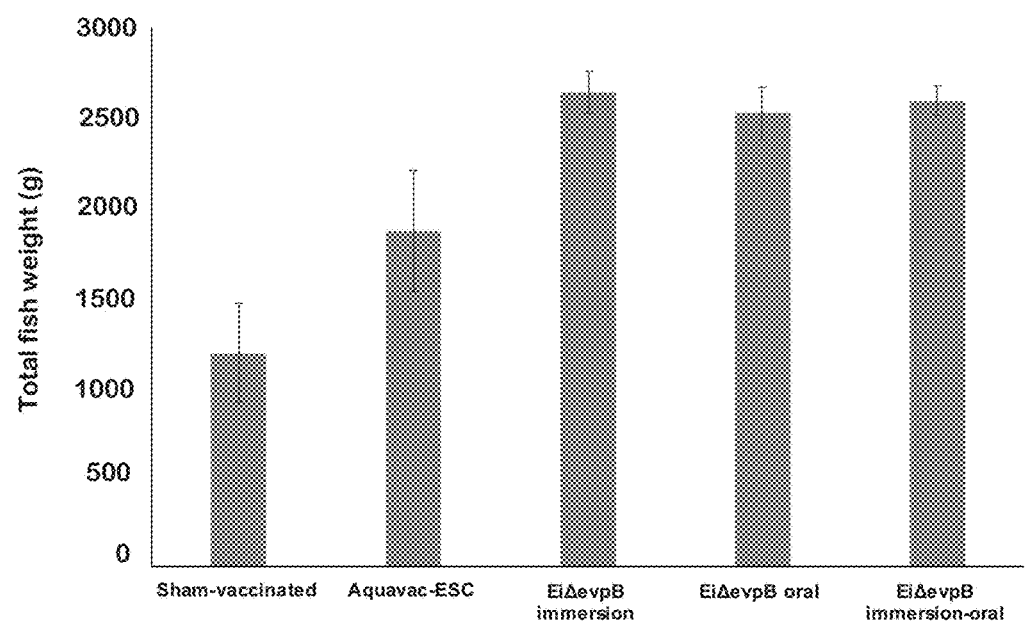
FIG. 9 is a bar graph showing the total weight of fish at harvest. This data represents the mean of four replicate pens in each pond.

Comparison of EiΔevpB to Commercial Vaccine AQUAVAC-ESC in Catfish Fry: Total Weight The mean total weight for each pen for fish vaccinated with EiΔevpB by immersion (2,630.75 g), oral (2,513 g), and immersion-oral combination (2,585.25 g) was significantly higher (p<0.05) than sham-vaccinated fish (1,186.5 g). No significant differences (p>0.05) in the total weight were observed between EiΔevpB vaccinated fish (immersion, oral, and immersion-oral combination) and AQUAVAC-ESC vaccinated fish (1861.75 g) (FIG. 9).

Example 11

Figure 10:
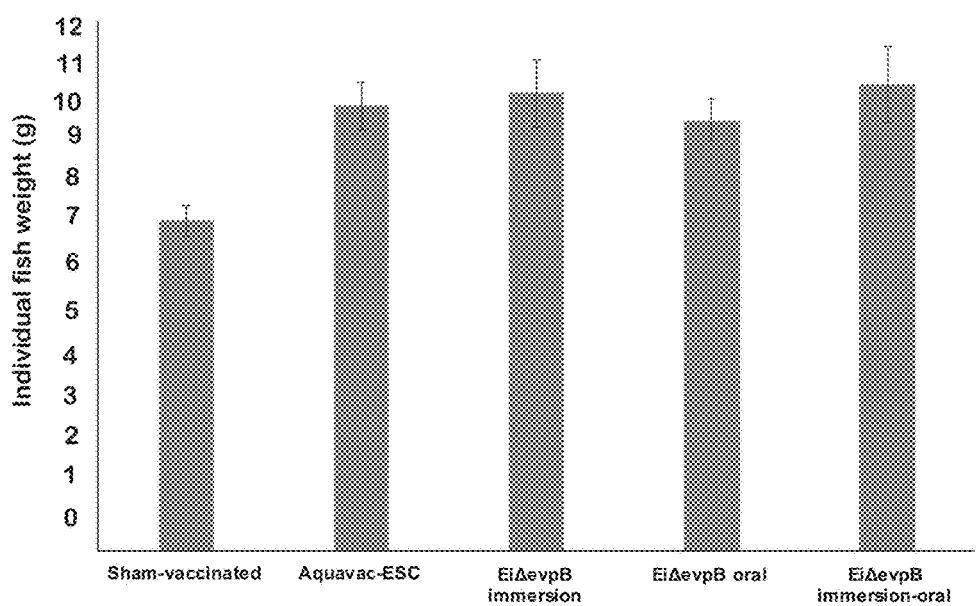
FIG. 10 is a bar graph showing the mean individual fish weight calculated from 30 fish from each of the four replicate pens in each pond.

Comparison of EiΔevpB to Commercial Vaccine AQUAVAC-ESC in Catfish Fry: Mean Individual Fish Weight The mean individual fish weights for 30 fish were 10.35, 9.73, 10.55, 10.06, and 7.48 g for immersion, oral, immersion-oral, AQUAVAC-ESC, and sham-vaccinated groups, respectively, (FIG. 10). Significantly higher individual fish weights were observed in the fish vaccinated with EiΔevpB by immersion and immersion-oral than sham-vaccinated pond (p<0.05). Whereas, no significant differences were noted between EiΔevpB oral vaccinated fish with sham-vaccinated pond.

Example 12

Figure 11:
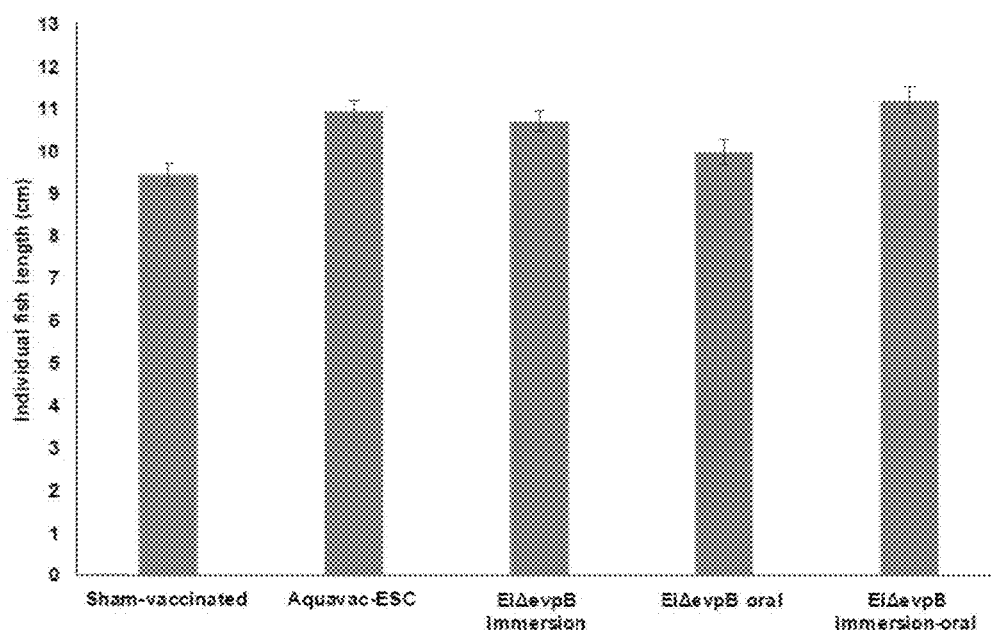
FIG. 11 is a bar graph showing the mean individual fish length calculated from 30 fish from each of the four replicate pens in each pond.

Comparison of EiΔevpB to Commercial Vaccine AQUAVAC-ESC in Catfish Fry: Mean Individual Fish Length Mean individual fish lengths for 30 fish were 10.69, 9.96, 11.20, 10.94, and 9.45 cm for immersion, oral, immersion-oral, AQUAVAC-ESC, and sham-vaccinated groups, respectively. The differences in individual fish lengths were not significantly different between the vaccinated fish (EiΔevpB and AQUAVAC-ESC), and sham control group (FIG. 11).

Discussion of Examples 8-12

In conclusion: The field trial supported previous laboratory results (above) that vaccination of channel catfish with EiΔevpB generated stronger protection against ESC compared to sham-vaccinated and AQUAVAC-ESC vaccinated fish.

Throughout this document, various references are mentioned. All such references are incorporated herein by reference, including the references set forth in the following list:

REFERENCES

1. Abdelhamed, H., Lu, J., Shaheen, A., Abbass, A., Lawrence, M. L., Karsi, A., 2013. Construction and evaluation of an *Edwardsiella ictaluri* fhuC mutant. Veterinary microbiology 162, 858-865.
2. Bertolini, J. M., Cipriano, R. C., Pyle, S. W., McLaughlin, J. J. A., 1990. SEROLOGICAL INVESTIGATION OF THE FISH PATHOGEN *EDWARDSIELLA ICTALURI*, CAUSE OF ENTERIC SEPTICEMIA OF CATFISH. Journal of Wildlife Diseases 26, 246-252.
3. Bingle, L. E., Bailey, C. M., Pallen, M. J., 2008. Type VI secretion: a beginner's guide. Current opinion in microbiology 11, 3-8.
4. Boyer, F., Fichant, G., Berthod, J., Vandenbrouck, Y., Attree, I., 2009. Dissecting the bacterial type VI secretion system by a genome wide in silico analysis: what can be learned from available microbial genomic resources? BMC genomics 10, 104.
5. Cascales, E., 2008. The type VI secretion toolkit, Vol 9, pp. 735-741
6. Dahal, N., Abdelhamed, H., Lu, J., Karsi, A., Lawrence, M. L., 2013. Tricarboxylic acid cycle and one-carbon metabolism pathways are important in *Edwardsiella ictaluri* virulence. PloS one 8, e65973.
7. Dozois, C. M., Daigle, F., Curtiss, R., 3rd, 2003. Identification of pathogen-specific and conserved genes expressed in vivo by an avian pathogenic *Escherichia coli* strain. Proceedings of the National Academy of Sciences of the United States of America 100, 247-252.
8. Ellis, A. E., (1988). Ontogeny of the Immune System in Teleost Fish. In: Ellis, A. E., Ed., Fish Vaccination, Academic Press, London, 20-31.
9. Filloux, A., Hachani, A., Bleves, S., 2008. The bacterial type VI secretion machine: yet another player for protein transport across membranes. Microbiology 154, 1570-1583.
10. Hawke, J. P., 1979. A Bacterium Associated with Disease of Pond Cultured Channel Catfish, *Ictalurus punctatus*. Journal of the Fisheries Research Board of Canada 36, 1508-1512.
11. Herrero, M., de Lorenzo, V., Timmis, K. N., 1990. Transposon vectors containing non-antibiotic resistance selection markers for cloning and stable chromosomal insertion of foreign genes in gram-negative bacteria. Journal of bacteriology 172, 6557-6567.
12. Horton, R. M., Cai, Z. L., Ho, S. N., Pease, L. R., 1990. Gene splicing by overlap extension: tailor-made genes using the polymerase chain reaction. BioTechniques 8, 528-535.
13. Karsi, A., Gulsoy, N., Corb, E., Dumpala, P. R., Lawrence, M. L., 2009. High-throughput bioluminescence-based mutant screening strategy for identification of bacterial virulence genes. Applied and environmental microbiology 75, 2166-2175.
14. Klesius, P. H., Shoemaker, C. A., 1997. Heterologous isolates challenge of channel catfish, *Ictalurus punctatus*, immune to *Edwardsiella ictaluri*. Aquaculture 157, 147-155.
15. Klesius, P. H., Shoemaker, C. A., 1999. Development and use of modified live *Edwardsiella ictaluri* vaccine against enteric septicemia of catfish. Advances in veterinary medicine 41, 523-537.
16. Lawrence, M. L., Cooper, R. K., Thune, R. L., 1997. Attenuation, persistence, and vaccine potential of an *Edwardsiella ictaluri* purA mutant. Infection and immunity 65, 4642-4651.

17. Lin, J. S., Ma, L. S., Lai, E. M., 2013. Systematic dissection of the agrobacterium type VI secretion system reveals machinery and secreted components for subcomplex formation. PloS one 8, e67647.
18. Miller, V. L., Mekalanos, J. J., 1988. A novel suicide vector and its use in construction of insertion mutations: osmoregulation of outer membrane proteins and virulence determinants in *Vibrio cholerae* requires toxR. Journal of bacteriology 170, 2575-2583.
19. Moore, M. M., Fernandez, D. L., Thune, R. L., 2002. Cloning and characterization of *Edwardsiella ictaluri* proteins expressed and recognized by the channel catfish *Ictalurus punctatus* immune response during infection. Diseases of aquatic organisms 52, 93-107.
20. Murdoch, S. L., Trunk, K., English, G., Fritsch, M. J., Pourkarimi, E., Coulthurst, S. J., 2011. The opportunistic pathogen *Serratia marcescens* utilizes type VI secretion to target bacterial competitors. Journal of bacteriology 193, 6057-6069.
21. Plumb, J. A., Sheifinger, C. C., Shryock, T. R., Goldsby, T., 1995. Susceptibility of Six Bacterial Pathogens of Channel Catfish to Six Antibiotics. Journal of Aquatic Animal Health 7, 211-217.
22. Plumb, J. A., Vinitnantharat, S., 1989. Biochemical, Biophysical, and Serological Homogeneity of *Edwardsiella ictaluri*. Journal of Aquatic Animal Health 1, 51-56.
23. Pukatzki, S., Ma, A. T., Sturtevant, D., Krastins, B., Sarracino, D., Nelson, W. C., Heidelberg, J. F., Mekalanos, J. J., 2006. Identification of a conserved bacterial protein secretion system in *Vibrio cholerae* using the Dictyostelium host model system. Proceedings of the National Academy of Sciences of the United States of America 103, 1528-1533.
24. Shoemaker, C. A., Klesius, P. H., Plumb, J. A., 1997. Killing of *Edwardsiella ictaluri* by macrophages from channel catfish immune and susceptible to enteric septicemia of catfish. Veterinary Immunology and Immunopathology 58, 181-190.
25. Shotts, E. B., Blazer, V. S., Waltman, W. D., 1986. Pathogenesis of Experimental *Edwardsiella ictaluri* Infections in Channel Catfish (*Ictalurus punctatus*). Canadian Journal of Fisheries and Aquatic Sciences 43, 36-42.
26. Silverman, J. M., Brunet, Y. R., Cascales, E., Mougous, J. D., 2012. Structure and regulation of the type VI secretion system. Annual review of microbiology 66, 453-472.
27. Smith, P., Hiney, M. P., Samuelsen, O. B., 1994. Bacterial resistance to antimicrobial agents used in fish farming: A critical evaluation of method and meaning. Annual Review of Fish Diseases 4, 273-313.
28. Srinivasa Rao, P. S., Yamada, Y., Tan, Y. P., Leung, K. Y., 2004. Use of proteomics to identify novel virulence determinants that are required for *Edwardsiella tarda* pathogenesis. Molecular Microbiology 53, 573-586.
29. Tatner, M. F., Manning, M. J., 1985. The ontogenetic development of the reticuloendothelial system in the rainbow trout, Salmo gairdneri Richardson. Journal of Fish Diseases 8, 189-195.
30. Thune, R. L., Collins, L. A., Penta, M. P., 1997. A Comparison of Immersion, Immersion/Oral Combination and Injection Methods for the Vaccination of Channel Catfish *Ictalurus punctatus* Against *Edwardsiella ictaluri*. Journal of the World Aquaculture Society 28, 193-201.
31. Williams, M. L., Gillaspy, A. F., Dyer, D. W., Thune, R. L., Waldbieser, G. C., Schuster, S. C., Gipson, J., Zaitshik, J., Landry, C., Banes, M. M., Lawrence, M. L., 2012. Genome Sequence of *Edwardsiella ictaluri* 93-146, a Strain Associated with a Natural Channel Catfish Outbreak of Enteric Septicemia of Catfish. Journal of bacteriology 194, 740-741.

We claim:

1. A vaccine for protecting fish against *Edwardsiella ictaluri* infection comprising an immunogenically effective amount of an attenuated *Edwardsiella ictaluri* bacterium, the bacterium lacking a viable gene encoding a functional EvpB protein by having a deletion of the coding sequence of the evpB gene.

2. A composition comprising an amount of live attenuated *Edwardsiella ictaluri* bacterium sufficient for protecting fish against infection from virulent *Edwardsiella ictaluri*, the bacterium lacking a viable gene encoding a functional EvpB protein by having a deletion of the coding sequence of the evpB gene, and one or more of the group consisting of a pharmaceutically-acceptable vehicle, a carrier, and an excipient.

3. The composition of claim 2, wherein the composition is formulated for delivery to fish by the method selected from the group consisting of an immersion delivery, an injection delivery, an oral delivery, or combinations thereof.

4. A method for protecting fish against infection from virulent *Edwardsiella ictaluri* comprising: administering to a fish a therapeutically effective amount of an attenuated *Edwardsiella ictaluri* bacterium lacking a viable gene encoding a functional EvpB protein by having a deletion of the coding sequence of the evpB gene.

5. The method of claim 4, wherein the administering step is selected from a group consisting of immersion delivery, injection delivery, oral delivery, and combinations thereof.

6. The method of claim 4, wherein the fish is a catfish.

7. The method of claim 4, wherein the attenuated *Edwardsiella ictaluri* bacterium is mixed with a fish feed to form a fish feed mixture, and wherein the fish feed mixture is delivered to the fish for oral consumption.

* * * * *

```
                         SEQUENCE LISTING

<160> NUMBER OF SEQ ID NOS: 5

<210> SEQ ID NO 1
<211> LENGTH: 29
<212> TYPE: DNA
<213> ORGANISM: Artificial Sequence
<220> FEATURE:
<223> OTHER INFORMATION: 1..2 Two adenosine nucleotides; 3..8 XbaI
      restriction site; 9..29 Edwardsiella ictaluri

<400> SEQUENCE: 1
aatctagagg acgactcacc tccgttatc                                 29

<210> SEQ ID NO 2
<211> LENGTH: 21
<212> TYPE: DNA
<213> ORGANISM: Edwardsiella ictaluri

<400> SEQUENCE: 2
tacgtcaccg gaaactgtca c                                         21

<210> SEQ ID NO 3
<211> LENGTH: 42
<212> TYPE: DNA
<213> ORGANISM: Edwardsiella ictaluri

<400> SEQUENCE: 3
```

```
gtgacagttt ccggtgacgt agatgtcagc gatattccag gt                              42

<210> SEQ ID NO 4
<211> LENGTH: 29
<212> TYPE: DNA
<213> ORGANISM: Artificial Sequence
<220> FEATURE:
<223> OTHER INFORMATION: 1..2 Two adenosine nucleotides; 3..8 XbaI
      restriction site; 9..29 Edwardsiella ictaluri

<400> SEQUENCE: 4
aatctagagt tgatcgctgt accgatgtc                                             29

<210> SEQ ID NO 5
<211> LENGTH: 20
<212> TYPE: DNA
<213> ORGANISM: Edwardsiella ictaluri

<400> SEQUENCE: 5
gcttcccaag ctgaaagaac                                                       20
```